United States Patent [19]
Katz

[11] Patent Number: 5,981,802
[45] Date of Patent: Nov. 9, 1999

[54] SIMPLE ALLYLIC AMINATION PROCEDURE

[75] Inventor: Thomas J. Katz, New York, N.Y.

[73] Assignee: The Trustees of Columbia University in the City of New York, New York, N.Y.

[21] Appl. No.: 08/572,573

[22] Filed: Dec. 14, 1995

[51] Int. Cl.$^6$ ................................................. C07C 209/44
[52] U.S. Cl. ......................................... 564/468; 564/488
[58] Field of Search ..................................... 564/468, 488

[56] References Cited

PUBLICATIONS

Brimble and Heathcock (1993) Allylic Amination by the Lewis–Acid–Mediated Ene Reaction of Diethyl Azodicarboxylate with Alkenes. *J. Org. Chem.* 58:5261–5263.

Bussas, R. and Kresze, G. (1982) Synthese von 2–Alkensulfinamiden–Struktur–Reactivitates–Beziehungen fur N–Sulfinylverbindungen als Enophile.

Deleris et al. (1988) Direct Regiospecific Allylic Aminaiton via Silicon Induced Pericyclic Reactions. A Novel Synthesis of Gamma Vinyl Gaba. *Tetrahedron* 44:4243–4258.

Garigipati et al. (1984) Diastereoselective systhesis of Unsaturated Vicinal Amino Alcohols via Diels–Alder Reactions of N–Sulfinyl Dienophiles. *J. Am. Chem. Soc.* 106:7861–7867.

Hancock, John and Markert, A.R. (1966) Azo and Hydrazo Compounds. III$^{1,2}$ Bis(Ethoxycarbonyl) Sulfurdiimine and Ethyl N–Sulfinyl Carbamate.

Hanson, P. and Stockburn, W.A. (1985) 1,2–Thiazines and Related Heterocycles. J. Chem. Soc., Perkin Trans. II pp. 589–595.

Hori, T. et al, (1978) Allylic Deuteration and Tritiation of Olefins With N–Sulfinylsulfonamides. *J. Org. Chem.* 43:1456–1459.

Johannsen, M and Jorgensen, K.A. (1994) Iron–Catalyzed Allylic Amination. *J. Org. Chem.* 59:214–216.

Katz, Thomas J. and Shi, Shuhao (1994) A Simple Allylic Amination Procedure and the Metathesis of N–Sulfinylcarbamates *J. Org. Chem.* 59:8297–8298.

Keck, Gary E. et al. (1981) A Versatile Method for Carbon–Nitrogen Bond Formation Via Ene Reactions of Acylnitrogen Compounds. *Tetrahedron* (23):4007–4016.

Kresze, G. and Munsterer, H., (1983) Bis(methoxycarbony)sulfur Diimide, a Convient Reagent for the Allylic Amination of Alkenes *J. Org. Chem.* 48:3561–3564.

Kresze, G. and Wucherpfennig, W. (1967) Organic Syntheses with Imides of Sulfur Dioxide. Angew. Chem. Int. Ed. Engl. 6(2):149–167.

Kresze, G. et al. (1993) *Organic Synthesis Collect.* vol. 8, pp. 427–430.

Levchenko, E.S. and Dorokhova, E.M. (1972) Derivatives of Thionyl Imide and Diiminosulfur. J. Org. Chem. USSR (Engl. Transl.) 8:2573–2577.

Levchencko, E.S., et al. (1967) Bisalkoxycarbonylsulfur Diimides. *J. Org. Chem. USSR* (*Engl. Transl.*) 3:2014–2019.

Minami, T. et al. (1968) The Chemistry of Cumulated Double Bond Compounds IV the Reaction of Sulfurdiimides With Triethylphosphite. *Tetrahedron Letters* 26:3049–3051.

Sharpless, K.B. and Hori, Tetsuo (1976) Allylic Amination of Olefins and Acetylenes by Imido Sulfur Compounds. *J. Org. Chem.* 41:176–177.

Singer, Stephen P. and Sharpless, K. Barry (1978) Synthesis of dl–Gabaculine Utilizing Direct Allylic Amination as the Key Step. *J. Org. Chem.* 43:1448–1455.

Whitesell, James K. and Yaser, H. Kenan (1991) Asymmetric Induction in Allylic Amination. J. Am. Chem. Soc. 113:3526–3529.

*Primary Examiner*—Brian M. Burn
*Attorney, Agent, or Firm*—John P. White; Cooper & Dunahm LLP

[57] ABSTRACT

The subject invention provides a method of preparing an allylic amine having the structure:

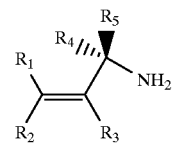

wherein $R_1$, $R_2$, $R_3$, $R_4$ and $R_5$ are each independently hydrogen, halogen, cyano, nitro, linear or branched chain alkyl, aryl, etc.; wherein each alkyl or arylalkyl if present is independently unsubstituted or substituted by fluoro, cyano, nitro, linear or branched chain acyl, dialkylamino, etc.; wherein each aryl if present is independently unsubstituted or substituted by fluoro, cyano, nitro, linear or branched chain alkyl, arylmercapto, etc.; and wherein each of $R_1$, $R_2$, $R_3$, $R_4$ and $R_5$ optionally is covalently bonded linking pairwise a suitable atom from each to form from 0 to about 10 rings, wherein each ring contains between about four and about twelve atoms, using disubstuted sulfur diimides prepared in situ. Also provided are methods of preparing cyclic allylic amines in which allylic double bonds are endocyclic and exocyclic.

26 Claims, 6 Drawing Sheets

SIMPLE ALLYLIC AMINATION PROCEDURE

This invention was made with government support under Grant No. CHE 92-24634 from the National Science Foundation. Accordingly, the U.S. Government has certain rights in the invention.

BACKGROUND OF THE INVENTION

Throughout this application, citations for various publications are provided in the text. The disclosures of these publications are hereby incorporated in their entirety by reference into this application in order to more fully describe the state of the art to which this invention pertains.

This invention relates to the field of allylic amination. More particularly, the invention relates to a simple procedure for directly preparing allylic amines from allylic compounds.

The subject invention provides a simple, efficient and inexpensive procedure for introducing an amino functionality into the allylic position of alkenes. The procedure is related to one developed by Kresze, et al. (Kresze, G., Munsterer, H., *J. Org. Chem.* 1983, 48, 3561). The subject invention shows how N,N'-bis-(alkoxy-carbonyl)sulfur diimides can be prepared easily, and how to overcome the large variability in yields of alkyl N-sulfinylcarbamates obtained when alkyl carbamates are combined with thionyl chloride in pyridine.

Figure 3:
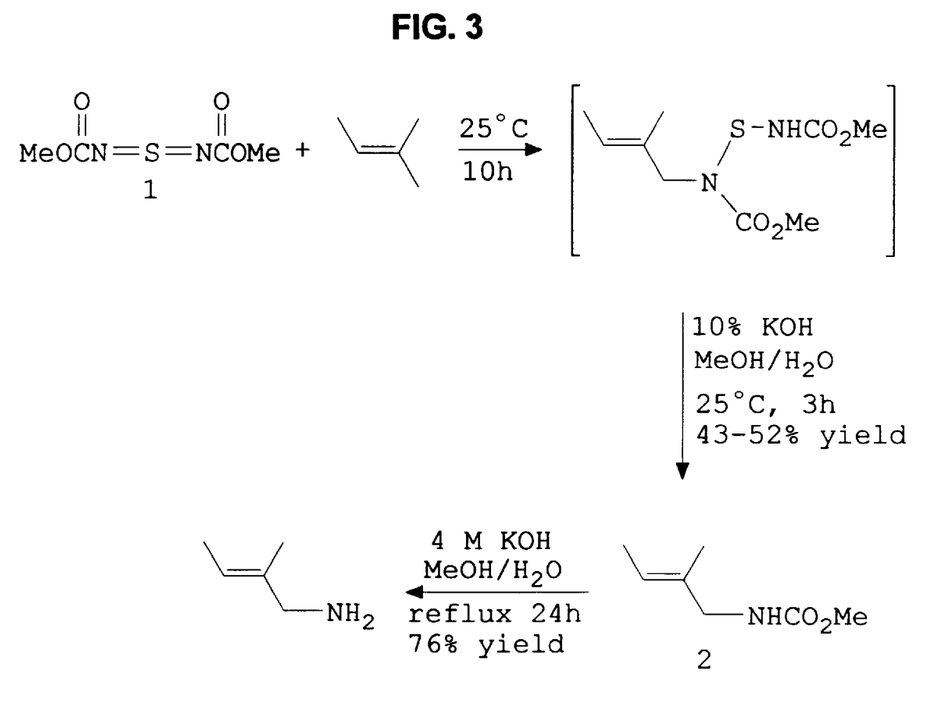
FIG. 3 shows a scheme for the preparation of allylic amines using previously prepared N,N'-bis(methoxycarbonyl)sulfur diimide.

The problem considered is that while N,N'-bis (methoxycarbonyl)sulfur diimide (1) has considerable benefit as a reagent to effect allylic aminations, e.g. FIG. 3 (Kresze, G., Münsterer, H., *J. Org. Chem.* 1983, 48, 3561), its preparation (FIG. 1), which calls for the manipulation of chlorine in both steps, is troublesome. Kresze, G., Braxmeier, H., Münsterer, H., *Organic Synthesis*; Wiley: New York, 1993; Collect. Vol. 8, p 427; Levchenko, E. S., Ballon, Ya, G., Kirsanov, A. V., *J. Org. Chem. USSR (Engl. Transl.)* 1967, 3, 2014. Thus, if diimide 1 could be obtained more easily, its usefulness for synthesis would increase significantly. The benefit of the scheme shown in FIG. 3 is the facility with which aqueous base removes residual groups from the nitrogen that is introduced, an advantage shared with a more lengthy procedure of Whitesell and Yaser that uses N-sulfinylcarbamates (Whitesell, J. K., Yaser, H. K., *J. Am. Chem. Soc.* 1991, 113, 3526) but not with those that effect allylic aminations by using reagents such as TsN=Se=NTs (Sharpless, K. B., Hori, T., Truesdale, L. K., Dietrich, C. O., *J. Am. Chem. Soc.* 1976, 98, 269), TsN=S=NTs (Sharpless, K. B., Hori, T., *J. Org. Chem.* 1976, 41, 176; Singer, S. P., Sharpless, K. B., *J. Org. Chem.* 1978, 43, 1448), PhSO$_2$NSO (Deleris, G., Dunogues, J., Gadras, A., *Tetrahedron*, 1988, 44, 4243), CH$_3$—OCON=NCOOCH$_3$ plus SnCl$_4$ (Brimble, M. A. Heathcock, C. H., *J. Org. Chem.* 1993, 58, 5261), AcNO (Keck, G. E., Webb, R. B., Yates, J. B., *Tetrahedron*, 1981, 37, 4007), and PhNHOH combined with transition-metal catalysts. (For example, see, Johannsen, M., Jørgensen, K. A., *J. Org. Chem.* 1994, 59, 214.) The leaving groups attached to nitrogen (ArSO$_2$, NHCO$_2$CH$_3$ or OH plus either Ac or Ph) are not readily removed by hydrolysis.

The amination method disclosed herein is useful for the preparation of biologically active allylic amines. An important application includes the synthesIs of certain allylic amine inhibitors of squalene epoxidase, which have powerful antifungal properties, and are useful in combatting fungal infections. Petraniy, G., Ryder, N. S., Stutz, A., *Science* (Washington, D.C.), 224, 1239 (1984). Accordingly, the subject method provides a route to prepare SF86-327, a powerful inhibitor of fungal squalene epoxidase. Petraniy, supra.

SUMMARY OF THE INVENTION

The subject invention relates to a method of preparing an allylic amine having the structure:

wherein R$_1$, R$_2$, R$_3$, R$_4$ and R$_5$ are each independently hydrogen, halogen, cyano, nitro, dialkylamino, alkoxy, aryloxy, alkoxycarbonyl, aryloxycarbonyl, alkylmercapto, arylmercapto, linear or branched chain alkyl, acyl, arylalkyl or aryl;

wherein each alkyl or arylalkyl if present is independently unsubstituted or substituted by fluoro, cyano, nitro, linear or branched chain acyl, dialkylamino, alkoxy, aryloxy, alkoxycarbonyl, aryloxycarbonyl, alkylmercapto, or arylmercapto;

wherein each aryl if present is independently unsubstituted or substituted by fluoro, cyano, nitro, linear or branched chain alkyl, acyl, dialkylamino, alkoxy, aryloxy, alkoxycarbonyl, aryloxycarbonyl, alkylmercapto, or arylmercapto;

wherein each of R$_1$, R$_2$, R$_3$, R$_4$ and R$_5$ optionally is covalently bonded linking pairwise a suitable atom from each to form from 0 to about 10 rings, wherein each ring contains between about four and about twelve atoms; which comprises:

(a) treating a compound having the structure:

with a sulfur diimide having the structure:

wherein R is substituted or unsubstituted linear or branched chain alkyl, arylalkyl or aryl; wherein the sulfur diimide used is formed in situ by reacting a primary carbamate having the structure:

with a thionyl halide having the formula SOM$_2$; wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

The present invention also provides a method of preparing an allylic amine having the structure:

wherein $R_1$, $R_2$ and $R_3$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl;

wherein $R_4$ and $R_5$ are each independently hydrogen, substituted or unsubstituted linear or branched chain alkyl or aryl; which comprises:

(a) reacting a compound having the structure:

with a sulfur diimide having the structure:

wherein R is substituted or unsubstituted, linear or branched chain alkyl, arylalkyl or aryl; wherein the sulfur diimide used is formed in situ by reacting a primary carbamate having the structure:

with a thionyl halide having the formula $SOM_2$; wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

The present invention provides a method of preparing an allylic amine having the structure:

wherein X, Y and Z are each independently C, N, O, S, Si or P; wherein $R_1$, $R_2$, $R_3$, $R_4$, $R_5$, $R_6$ and $R_7$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl;

wherein when X is O or S, $R_2$ and $R_3$ are absent; wherein when Y is O or S, $R_4$ and $R_5$ are absent; wherein when Z is O or S, $R_6$ and $R_7$ are absent; wherein when X is N or P, $R_2$ is absent; wherein when Y is N or P, $R_4$ is absent; wherein when Z is N or P, $R_6$ is absent; wherein i, j and k are each independently an integer between about 0 and about 6; wherein i+j+k is from 1 to about 8;

wherein $R_8$ and $R_9$ are each independently hydrogen, substituted or unsubstituted linear or branched chain alkyl or aryl; which comprises:

(a) treating a compound having the structure:

with a sulfur diimide having the structure:

wherein R is substituted or unsubstituted linear or branched chain alkyl, arylalkyl or aryl; wherein the sulfur diimide used is formed in situ by reacting a primary carbamate having the structure:

with a thionyl halide having the formula $SOM_2$; wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

The subject invention also provides a method of preparing an allylic amine having the structure:

wherein X, Y and Z are each independently C, N, O, S, Si or P; wherein $R_1, R_2, R_3, R_4, R_5, R_6, R_7$ and $R_8$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl; wherein when X is N or P, $R_1$ is absent; wherein when Y is N or P, $R_3$ is absent; wherein when Z is N or P, $R_5$ is absent; wherein when X is O or S, $R_1$ and $R_2$ are absent; wherein when Y is O or S, $R_3$ and $R_4$ are absent; wherein when Z is O or S, $R_5$ and $R_6$ are absent; wherein i, j and k are each independently an integer between about 0 and about 6; wherein i+j+k is from 1 to about 8;

wherein $R_9$ is hydrogen, substituted or unsubstituted linear or branched chain alkyl and aryl; which comprises:

(a) reacting a compound having the structure:

with a sulfur diimide having the structure:

wherein R is substituted or unsubstituted linear or branched chain alkyl, arylalkyl or aryl; wherein the sulfur diimide is formed in situ by reacting a primary carbamate having the structure:

with a thionyl halide having the formula $SOM_2$, wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

DETAILED DESCRIPTION OF THE INVENTION

The subject invention provides a method of preparing an allylic amine having the structure:

wherein $R_1$, $R_2$, $R_3$, $R_4$ and $R_5$ are each independently hydrogen, halogen, cyano, nitro, dialkylamino, alkoxy, aryloxy, alkoxycarbonyl, aryloxycarbonyl, alkylmercapto, arylmercapto, linear or branched chain alkyl, acyl, arylalkyl or aryl;

wherein each alkyl or arylalkyl if present is independently unsubstituted or substituted by fluoro, cyano, nitro, linear or branched chain acyl, dialkylamino, alkoxy, aryloxy, alkoxycarbonyl, aryloxycarbonyl, alkylmercapto, or arylmercapto;

wherein each aryl if present is independently unsubstituted or substituted by fluoro, cyano, nitro, linear or branched chain alkyl, acyl, dialkylamino, alkoxy, aryloxy, alkoxycarbonyl, aryloxycarbonyl, alkylmercapto, or arylmercapto;

wherein each of $R_1$, $R_2$, $R_3$, $R_4$ and $R_5$ optionally is covalently bonded linking pairwise a suitable atom from each to form from 0 to about 10 rings, wherein each ring contains between about four and about twelve atoms; which comprises:

(a) treating a compound having the structure:

with a sulfur diimide having the structure:

wherein R is substituted or unsubstituted linear or branched chain alkyl, arylalkyl or aryl; wherein the sulfur diimide used is formed in situ by reacting a primary carbamate having the structure:

with a thionyl halide having the formula SOM$_2$; wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

Step (a) is carried out in an inert organic solvent such as diethyl ether at low temperatures ranging from −20° C. to +35° C., but preferably from 0° C. to +25° C. The process is continued by removal of the solvent by any method known in the art, including rotary evaporation, and the residue is heated at elevated temperatures ranging from +45° C. to +90° C., but preferably from +60° C. to +80° C. An allylic compound is added in an inert organic solvent such as chloroform at low temperatures ranging from −15° C. to +30° C., but preferably from 0° C. to +25° C.

Step (b) is performed using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between one and 25% by weight, but preferably at 10% by weight, at temperatures ranging from +5° C. to +30° C., but preferably from +20° C. to +25° C.

Step (c) is effected using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between 0.5M and 5M, but preferably at 4M, at temperatures ranging from +45° C. to +120° C., but preferably from +90° C. to +105° C.

In one embodiment, the present invention provides the method as disclosed hereinabove wherein M is Cl and R is methyl.

In another embodiment, the present invention provides the method as disclosed hereinabove wherein the base is an organic amine.

In another embodiment, the present invention provides the method as disclosed hereinabove wherein the organic amine is pyridine.

In yet another embodiment, the present invention provides the method as disclosed hereinabove wherein the organic amine is present in a 102 to 125 mole percent excess with respect to the primary carbamate.

In another embodiment, the present invention provides the method as disclosed hereinabove wherein the organic amine is present in a 105 mole percent excess with respect to the primary carbamate.

The present invention also provides a method of preparing an allylic amine having the structure:

wherein $R_1$, $R_2$ and $R_3$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl;

wherein $R_4$ and $R_5$ are each independently hydrogen, substituted or unsubstituted linear or branched chain alkyl or aryl; which comprises:

(a) reacting a compound having the structure:

with a sulfur diimide having the structure:

wherein R is substituted or unsubstituted, linear or branched chain alkyl, arylalkyl or aryl; wherein the sulfur diimide used is formed in situ by reacting a primary carbamate having the structure:

with a thionyl halide having the formula $SOM_2$; wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

Step (a) is carried out in an inert organic solvent such as diethyl ether at low temperatures ranging from −20° C. to +35° C., but preferably from 0° C. to +25° C. The process is continued by removal of the solvent by any method known in the art, including rotary evaporation, and the residue is heated at elevated temperatures ranging from +45° C. to +90° C., but preferably from +60° C. to +80° C. An allylic compound is added in an inert organic solvent such as chloroform at low temperatures ranging from −15° C. to +30° C., but preferably from 0° C. to +25° C.

Step (b) is performed using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between one and 25% by weight, but preferably at 10% by weight, at temperatures ranging from +5° C. to +30° C., but preferably from +20° C. to +25° C.

Step (c) is effected using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between 0.5M and 5M, but preferably at 4M, at temperatures ranging from +45° C. to +120° C., but preferably from +90° C. to +105° C.

In a certain embodiment, the present invention provides the method as disclosed hereinabove wherein M is Cl and R is methyl.

In another embodiment, the present invention provides the method as disclosed hereinabove wherein the base is an organic amine.

In yet another embodiment, the present invention provides the method as disclosed hereinabove wherein the organic amine is pyridine.

In another embodiment, the present invention provides the method as disclosed hereinabove wherein the organic amine is present in a 102 to 125 mole percent excess with respect to the primary carbamate.

In still another embodiment, the present invention provides the method as disclosed hereinabove wherein the organic amine is present in a 105 mole percent excess with respect to the primary carbamate.

The present invention provides a method of preparing an allylic amine having the structure:

wherein X, Y and Z are each independently C, N, O, S, Si or P; wherein $R_1$, $R_2$, $R_3$, $R_4$, $R_5$, $R_6$ and $R_7$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl; wherein when X is O or S, $R_2$ and $R_3$ are absent; wherein when Y is O or S, $R_4$ and $R_5$ are absent; wherein when Z is O or S, $R_6$ and $R_7$ are absent; wherein when X is N or P, $R_2$ is absent; wherein when Y is N or P, $R_4$ is absent; wherein when Z is N or P, $R_6$ is absent; wherein i, j and k are each independently an integer between about 0 and about 6; wherein i+j+k is from 1 to about 8;

wherein $R_8$ and $R_9$ are each independently hydrogen, substituted or unsubstituted linear or branched chain alkyl or aryl; which comprises:

(a) treating a compound having the structure:

with a sulfur diimide having the structure:

wherein R is substituted or unsubstituted linear or branched chain alkyl, arylalkyl or aryl; wherein the sulfur diimide used is formed in situ by reacting a primary carbamate having the structure:

with a thionyl halide having the formula $SOM_2$; wherein M is Br, Cl, F or I, in the presence of a base, to form an intermediate;
(b) hydrolyzing the intermediate formed in step (a) to form an allylic carbamate having the structure:

and
(c) saponifying and decarboxylating the allylic carbamate formed in step (b) to form the allylic amine.

Step (a) is carried out in an inert organic solvent such as diethyl ether at low temperatures ranging from −20° C. to +35° C., but preferably from 0° C. to +25° C. The process is continued by removal of the solvent by any method known in the art, including rotary evaporation, and the residue is heated at elevated temperatures ranging from +45° C. to +90° C., but preferably from +60° C. to +80° C. An allylic compound is added in an inert organic solvent such as chloroform at low temperatures ranging from −15° C. to +30° C., but preferably from 0° C. to +25° C.

Step (b) is performed using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between one and 25% by weight, but preferably at 10% by weight, at temperatures ranging from +5° C. to +30° C., but preferably from +20° C. to +25° C.

Step (c) is effected using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between 0.5M and 5M, but preferably at 4M, at temperatures ranging from +45° C. to +120° C., but preferably from +90° C. to +105° C.

In one embodiment, the present invention provides a method as disclosed hereinabove wherein X, Y and Z are C.

In another embodiment, the present invention provides the method as disclosed hereinabove wherein M is Cl and R is methyl.

In yet another embodiment, the present invention provides the method as disclosed hereinabove wherein the base is an organic amine.

In another embodiment, the present invention provides the method as disclosed hereinabove wherein the organic amine is pyridine.

In still another embodiment, the present invention provides the method as disclosed hereinabove wherein the organic amine is present in a 102 to 125 mole percent excess with respect to the primary carbamate.

In another embodiment, the present invention provides the method as disclosed hereinabove wherein the organic amine is present in a 105 mole percent excess with respect to the primary carbamate.

The present invention further provides a method of preparing an allylic amine having the structure:

wherein X, Y and Z are each independently C, N, O, S, Si or P; wherein $R_1, R_2, R_3, R_4, R_5, R_6, R_7$ and $R_8$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl; wherein when X is N or P, $R_1$ is absent; wherein when Y is N or P, $R_3$ is absent; wherein when Z is N or P, $R_5$ is absent; wherein when X is O or S, $R_1$ and $R_2$ are absent; wherein when Y is O or S, $R_3$ and $R_4$ are absent; wherein when Z is O or S, $R_5$ and $R_6$ are absent; wherein i, j and k are each independently an integer between about 0 and about 6; wherein i+j+k is from 1 to about 8;

wherein $R_9$ is hydrogen, substituted or unsubstituted linear or branched chain alkyl and aryl; which comprises:

(a) reacting a compound having the structure:

with a sulfur diimide having the structure:

wherein R is substituted or unsubstituted linear or branched chain alkyl, arylalkyl or aryl; wherein the sulfur diimide used is formed in situ by reacting a primary carbamate having the structure:

with a thionyl halide having the formula $SOM_2$; wherein M is Br, Cl, F or I, in the presence of a base, to form an intermediate;
(b) hydrolyzing the intermediate formed in step (a) to form an allylic carbamate having the structure:

and
(c) saponifying and decarboxylating the allylic carbamate formed in step (b) to form the allylic amine.

Step (a) is carried out in an inert organic solvent such as diethyl ether at low temperatures ranging from −20° C. to +35° C., but preferably from 0° C. to +25° C. The process is continued by removal of the solvent by any method known in the art, including rotary evaporation, and the residue is heated at elevated temperatures ranging from +45° C. to +90° C., but preferably from +60° C. to +80° C. An allylic compound is added in an inert organic solvent such as chloroform at low temperatures ranging from −15° C. to +30° C., but preferably from 0° C. to +25° C.

Step (b) is performed using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between one and 25% by weight, but preferably at 10% by weight, at temperatures ranging from +5° C. to +30° C., but preferably from +20° C. to +25° C.

Step (c) is effected using a strong base such as sodium hydroxide, potassium hydroxide or lithium hydroxide in an aqueous solvent system incorporating a miscible polar organic such as methanol, isopropanol or ethanol, wherein the base is initially dissolved in the aqueous component at concentrations of between 0.5M and 5M, but preferably at 4M, at temperatures ranging from +45° C. to +120° C., but preferably from +90° C. to +105° C.

In a certain embodiment, the present invention provides the method as disclosed hereinabove wherein X, Y and Z are C.

In another embodiment, the present invention provides the method as disclosed hereinabove wherein M is Cl and R is methyl.

In still another embodiment, the present invention provides the method as disclosed hereinabove wherein the base is an organic amine.

In a further embodiment, the present invention provides the method as disclosed hereinabove wherein the organic amine is pyridine.

In another embodiment, the present invention provides the method as disclosed hereinabove wherein the organic amine is present in a 102 to 125 mole percent excess with respect to the primary carbamate.

In yet another embodiment, the present invention provides the method as disclosed hereinabove wherein the organic amine is present in a 105 mole percent excess with respect to the primary carbamate.

The method provided herein is also applicable to prepare multi-ring allylic amines wherein each ring is optionally fused to one or more other rings each independently of four to twelve atoms; and wherein each ring fusion independently contains 0, 1, 2, 3, or 4 bridging atoms. One of ordinary skill in the art will understand that energetic constraints dictate the stereochemical nature of each ring fusion as well as the overall stability of each compound. Among the chemical factors which determine the stability of particular multi-ring allylic amines are the multiplicity and steric bulk of substituents, orbital overlap, ring strain and noncovalent interactions. T. H. Lowry and K. S. Richardson, *Mechanism and Theory in Organic Chemistry*, 3d ed., Harper & Row, New York, 1987.

As used herein, the term "allylic compound" encompasses, but is not limited to, alkyl, aryl or cycloalkyl compounds containing at least one allylic moiety. If cycloalkyl, the compound may consist of one or more rings, usually between one to six rings, and if more than one ring, the rings of the compound may be linked via a single atom in each ring, or fused via two atoms in each ring, or fused via one atom common to two rings. Rings may be fused in a linear or branched manner to one or more other rings, and may be fully saturated, or partially or fully unsaturated.

In referring to cycloalkyl compounds, the term "allylic compound", as used herein, includes structures containing an allylic double bond either endocyclic or exocyclic with respect to the cycloalkyl ring. Furthermore, the cycloalkyl compound may contain one or more heteroatoms, including, but not limited to, N, O, S, Si, P, Sn, Ge, Te, Se and Pb, and may also contain one or more carbonyl groups.

When substituted, substituents of the allylic compound include, but are not limited to, one or more of the following groups: halogens (F, Br, Cl, I) , linear or branched alkyl, linear or branched acyl, linear or branched perfluoroalkyl, alkoxy, amino, alkylamino, dialkylamino, trialkylammonium, dialkylammonium, monoalkyldiaylammonium, carboxyl, alkoxycarbonyl, aryloxycarbonyl, carboxamido, (N-alkyl)carboxamido, (N,N-dialkyl) carboxamido, (N-aryl)carboxamido, (N,N-diaryl) carboxamido, sulfonamido, (N-alkyl) sulfonamido, sulfonate, phosphate, cyano, acetylene, nitro, nitrose, azido, cyanoalkyl, nitroalkyl, nitrosoalkyl, azidoalkyl, alkoxyalkyl, mercapto, thioketone, formyl, formylalkyl, alkylmercapto, arylmarcapto, mercaptoalkyl, alkyldiazo, alkyldiazoalkyl, aryldiazo, aryldiazoalkyl, carboxyalkyl, hydroxy, hydroxyalkyl, aminoalkyl, alkylaminoalkyl, dialkylamino alkyl, trialklammonium alkyl, dialklyarylammonium alkyl and monoalkyldiarylammonium alkyl.

Certain specific substituents of the allylic compound include, but are not limited to, acetyl, propionyl, butyryl, pentanyl, benzyl, tolyl, 2-hydroxyethyl, hydroxymethyl, 2- or 3-hydroxypropyl, aminomethyl, 2-aminoethyl, 2- or 3-aminopropyl, methoxymethyl, methoxyethyl, ethoxymethyl, ethoxypropyl, carbomethoxy, carboethoxy, carbomethoxymethyl, carboxamidomethyl, carboxamidoethyl, benzyl, phenyl, ethylphenyl, dimethylphenyl, trimethylphenyl, tetramethylphenyl, pentamethylphenyl, fluorophenyl, dichlorophenyl, triiodophenyl, tetrafluorophenyl, pentachlorophenyl, methoxyphenyl, 2-methyl-3-methoxyphenyl, cyanophenyl, aminophenyl, 3-(N-methylamino)phenyl, carboxamidophenyl, hydroxyphenyl, dihydroxyphenyl, naphthyl, anthracenyl, indolyl, thiophene, tetrahydrofuranyl, tetrahydropyranyl, pyrrolyl, and pyridyl.

In addition, the subject method provides a route to prepare SF86-327, a powerful inhibitor of fungal squalene epoxidase. Petraniy, supra. Thus, in one embodiment, application of the subject method to 4-(dimethyl)hepten-1-yne-3 provides the corresponding allylic amine. Sequential alkylation of the resulting allylic amine with bromomethylnapthalene, followed by methyl iodide, generates SF86-327.

The following Experimental Details are set forth to aid in an understanding of the invention, and are not intended, and should not be construed, to limit in any way the invention set forth in the claims which follow thereafter.

Experimental Details

EXAMPLE 1

Amination of 2-Methyl-2-butene. Pyridine (65.0 g, 0.823 momol) was added in drops during a period of 0.5 h to a solution of methyl carbamate (30.0 g, 0.400 mol) and $SOCl_2$ (47.6 g, 0.400 mol) in 500 mL of ether that was cooled in an ice bath and stirred. The bath was removed, and stirring was continued for 4 h. After the pyridine hydrochloride had been filtered and washed quickly with ether, the solvent was evaporated and the residue was heated at 60–80° C. for 30 min. Any N-sulfinylcarbamate present was then removed by evacuating the flask to a pressure of 0.5 mmHg for 10 min. (In a repetition of the experiment, the yield of methyl N-sulfinylcarbamate that could be distilled from the product was <4%.) The reaction with 14.1 g (0.20 mol) of 2-methyl-2-butane was carried out exactly as in Kresze, G., Braxmeier, H., Munsterer, H., Org. Synth., 1993, Coll. Vol. 8, 427. The yield of distilled 2 was 12.4 g (43% yield). A similar experiment that started with 7.5 g of methyl carbamate gave 3.38 g of 2 (a 47% yield). Its NMR spectra match those reported: $^{13}C$ NMR (75 MHz, $CDCl_3$) δ 13.2, 14.0, 48.6, 52.0, 120.5, 132.7, 157.3; $^1H$ NMR (400 MHz, $CDCl_3$) δ 1.59 (d, q, J=ca. 6.5, 1.1 Hz, 3H), 1.61 (be, 3H), 3.67 (s, 3H), 3.69 (d, J=5.8 Hz, 2H), 4.68 (bs, 1H), 5.39 (q, J=6.4, 1H); MS (EI) m/z (rel intensity) 143 (30), 135 (100), 128 (26), 102 (20), 76 (100), 69 (42), 59 (78), 42 (34), HRMS (EI) calcd for $C_7H_{13}NO_2$ 143.0946, found 143.0940.

EXAMPLE 2

Preparation of Methyl N-Sulfinylcarbamate. Pyridine (15.2 g, 0.192 mol) in 50 mL of ether was added in drops during a period of 1.5 h to a stirred solution of 7.5 g (0.100 mol) of methyl carbamate and 13.1 g (0.110 mol) of $SOCl_2$ in 250 mL of ether, and the mixture was stirred for another 1.5 h. After the pyridine hydrochloride had been filtered and washed quickly with ether, the solvent was stripped, and the residue was distilled (ca. 31°C./2 mmHg) to a receiver cooled in dry ice-acetone. Obtained was 9.5 g of colorless liquid, analyzed by its proton NMR spectrum to be a mixture of 8.8 g of methyl N-sulfinylcarbamate (a 76% yield) and 0.76 g (a 10% recovery) of methyl carbamate. $^1H$ NMR spectra in $CDCl_3$: methyl N-sulfinylcarbamate, δ 3.95; methyl carbamate, δ3.69.

When the amounts of methyl carbamate, thionyl chloride, and pyridine were 7.50 g (0.100 mol), 11.90 g (0.100 mol), and 15.01 g (0.190 mol), the distillate obtained consisted of 5.9 g of methyl N-sulfinylcarbamate (a 51% yield) and 0.5 g of recovered methyl carbamate. The same experiment, but using 16.59 g of pyridine (0.210 mol), gave only 0.5 g of distillate, which $^1H$ NMR analysis showed to be a mixture of methyl carbamate (δ3.69), 1 (δ 3.87), methyl N-sulfinylcarbamate (δ 3.95), and pyridine [δ 8.05 (t), 8.50 (t), and 8.94 (d)]. The yield of methyl N-sulfinylcarbamate was thus <0.5 g (4%). In these experiments, the reaction mixture was cooled in an ice bath while the pyridine was added, then the solution was stirred for 1–1.5 h at room temperature and worked up as before.

Conversion of Methyl N-Sulfinylcarbamate into $N,N^1$-Bis (methoxycarbonyl)sulfur Diimide (1). Samples in $CDCl_3$ of methyl N-sulfinylcarbamate (1 g) stirred with pyridine (40 mg) were analyzed by $^1H$ NMR spectroscopy (starting material, δ 3.95; product sulfur diimide, δ 3.87 (reported in Kresze, G., Munsterer, H., J. Org. Chem. 1983, 48, 3561, δ 3.88). After 1 h at 60–80° C., the conversion was 67%, and after 3 h, 83%. After 4 h at room temperature, the conversion was 50%, and after 14 h, 64%.

Results and Discussion

Practice of the subject invention required determination of whether 1 can be obtained by the same procedure (FIG. 2) that converts TsNSO into TSN=S=NTs. Wucherpfennig, W., Kresze, G., Tetrahedron Lett. 1988, 1671; Kresze, G., Wucherpfennig, W., Angew. Chem. Int. Ed. Engl. 1967, 6, 149 (see p 165); Bussas, R., Kresze, G. Liebigs Ann. Chem. 1980, 629. Pyridine also converts PhCONSO into PhCON-SNCOPh (Levchencko, E. S., Dorokhova, E. M., J. Org. Chem. USSR (Engl. Transl.) 1972, 8, 2573), while metal alkoxides and other strong bases similarly convert arylN-SO's. Hörhold, H.-H., Z. Chem. 1972, 12, 41; Hörhold, H.-H., Flossman, K.-D., Z. Chem. 1967, 7, 345; Minami, T., Miki, H., Matsumoto, H., Ohshiro, Y., Agawa, T., Tetrahedron Lett. 1968, 3049; Hörhold, H.-H., Beck, J., J. Prakt. Chem. 1969, 311, 621. Piperidine condenses arylNSO's with aldehydes. Hörhold, H. H., Z. Chem. 1972, 12, 41. Accordingly, the only reagents required to effect an allylic amination, such as that in FIG. 3, would be methyl carbamate, thionyl chloride, and pyridine. (N-Sulfinylcarbamates are prepared by combining carbamates with SOCl$_2$ in pyridine. Hancock, J., Markert, A. R., *Tetrahedron Lett.* 1966, 6157; Kresze, G., Wucherpfennig, W., *Angew. Chem., Int. Ed. Engl.* 1967, 6, 149ff.

Figure 1:
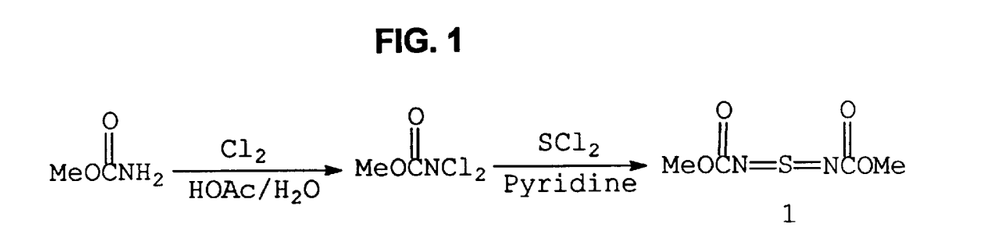
FIG. 1 shows a scheme for the preparation of allylic amines using the method of Kresze, et al.
Figure 4:
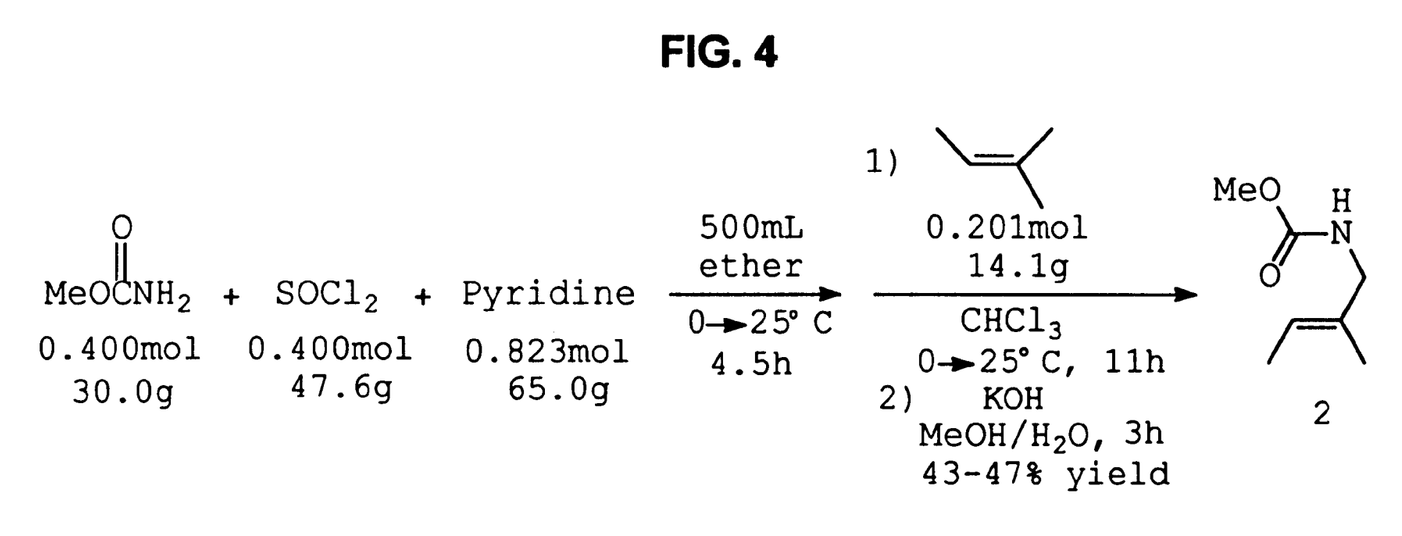
FIG. 4 shows a scheme for the preparation of allylic amines using N,N'-bis(methoxycarbonyl)sulfur diimide prepared in situ.

The result was that this combination (FIG. 4) does indeed bring about allylic amination more easily and efficiently than when FIG. 3 follows FIG. 1. Kresze, G., Münsterer, H., *J. Org. Chem.* 1983, 48, 3561. (The yield of 2 in FIG. 3 is based on the amount of dichlorocarbamate used to make 1. Dichlorocarbamate was made from the carbamate in 63–73% yield.) Moreover, minute amounts of pyridine at 60–80° C. (and at room temperature more slowly) do convert MeOCONSO into MeOCON=S=NCOOMe (FIG. 2; X=CO$_2$Me).

This conversion has another previously unrecognized consequence. It explains why the yields obtained in reported N-sulfinylations vary without apparent reason and what must be done to obtain yields that are consistently satisfactory. Since pyridine catalyzes the conversion of MeOCONSO into MeOCON=S=NCOOMe, to obtain MeOCONSO in good yield (FIG. 5), it is essential that pyridine, a reagent in the preparation, not be present in excess. (The best yields of distilled N-sulfinylcarbamate (73%), contaminated by 10% recovered methyl carbamate, were obtained by using a small deficiency of pyridine and a small excess of thionyl chloride.)

Figure 6:
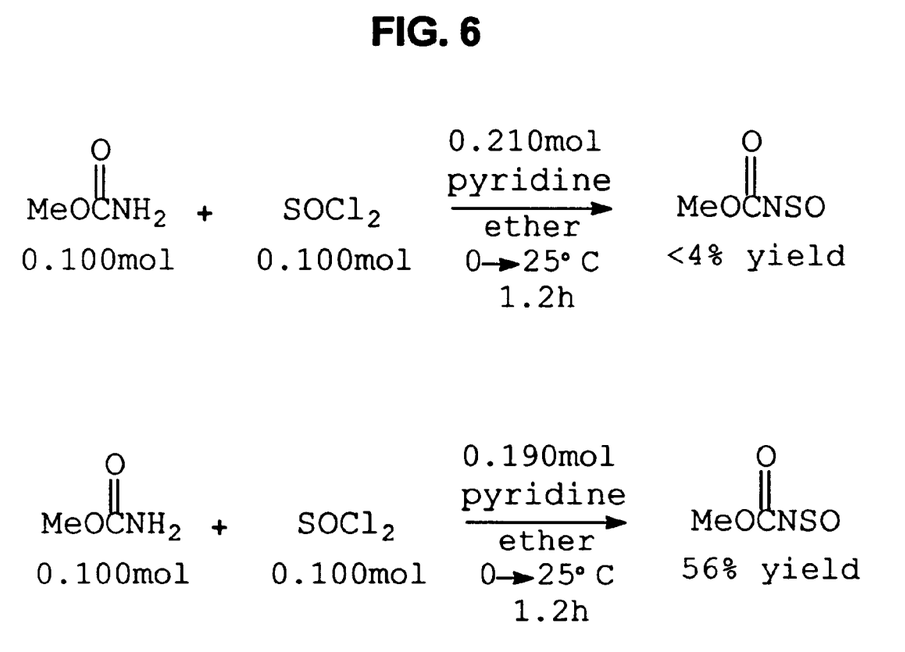
FIG. 6 shows the effect of varying the relative proportion of pyridine on the preparation of MeO$_2$CNSO from methyl carbamate, thionyl chloride and pyridine.

The equations in FIG. 6 demonstrate the difference that is observed when methyl carbamate, thionyl chloride, and pyridine are combined in ca. 1:1:2 molar ratios, but with slightly less than 2 mol of pyridine in the one case and slightly more in the other. If there is 5% too much pyridine, the yield of N-sulfinylcarbamate is essentially nil. Ichimura, et al. and subsequently Bussas and Kresze recorded the need for modified procedures. Ichimura, K., Ichikawa, S., Imamura, K., *Bull. Chem. Soc. Jpn.* 1976, 49, 1157; Bussas, R., Kresze, G., *Liebigs. Ann. Chem.* 1982, 545. Ichimura, K., et al. report that yields are poor when SOCl$_2$ is added to the carbamate and pyridine but good when SOCl$_2$ and pyridine are added in drops to the carbamate. In addition, Hanson and Stockburn, whose procedure recites the use of 2–6% less pyridine than required by the other reagents, obtained a yield of 75%. Hanson, P., Stockburn, W. A., *J. Chem. Soc.*, Perkin Trans. 2, 1985, 589. The yield reported by Hanson and Stockburn (94%) was miscalculated. Hancock and Markert (who did not specify how much pyridine they used) obtained a yield of only 20%. (Hancock, J., Markert, A. R., *Tetrahedron Lett.* 1966, 6157) Nevertheless, the essential principle has heretofore remained obscure.

Other protocols also require use of a deficiency of pyridine and addition thereof last (Garigipati, R. S., Freyer, A. J., Whittle, R. R., Weinreb, S. M., *J. Am. Chem. Soc.* 1984, 106, 7861; Wald, L., Wucherpfennig, W., *Liegigs Ann. Chem.* 1971, 746, 28; Niclas, H.-J., Habisch, D., Martin, D. *Tetrahedron* 1979, 35, 2353), although one is accompanied by a preparation in which the pyridine is added first. Wald, L., Wucherpfennig, W., *Liebigs Ann. Chem.* 1971, 746, 28. Whitesell and Yaser used an excess of SOCl$_2$. Whitesell, J. K., Yaser, H. K., *J. Am. Chem. Soc.* 1991, 113, 3526. It is noteworthy that the preparation of TsNSO from TsNH$_2$ and SOCl$_2$ requires no pyridine, although the reaction time can be very long. Kresze, G., Wucherpfennig, W., *Angew. Chem. Int. Ed. Engl.* 1967, 6, 149 (see p 151); Hori, T., Singer, S. P., Sharpless, K. B., *J. Org. Chem.* 1978, 43, 1456. The scientific problem solved by the subject invention is reminiscent of that presented by the synthesis of cyanohydrins before 1903, when it was not recognized that an extra drop of H$_2$SO$_4$, beyond that needed to neutralize the cyanide salts, is deleterious. Lapworth, A., *J. Chem. Soc.* 1903, 83, 995 ("It is probably a general experience that in preparing cyanohydrin . . . the speed of the reaction and the yield . . . obtained may vary in an extraordinary manner, even when the experimental conditions are apparently constant . . .")

Figure 2:
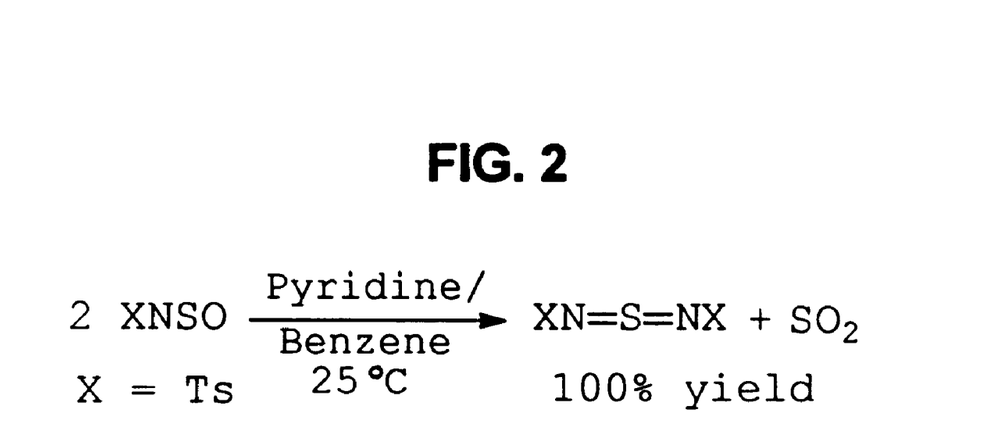
FIG. 2 shows a scheme for the preparation of bis(p-toluenasulonyl)sulfur diimide using pyridine.
Figure 5:
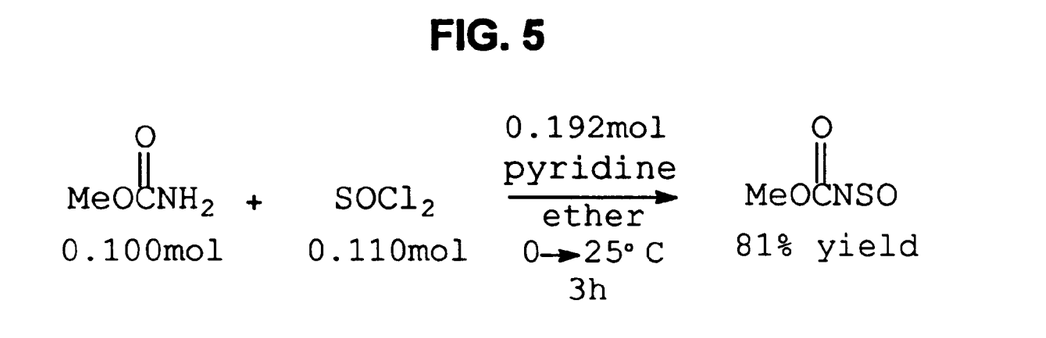
FIG. 5 shows a reaction to prepare MeO$_2$CNSO, an intermediate used in the preparation of N,N'-bis(methoxycarbonyl)sulfur diimide.

The invention disclosed herein demonstrates three points: that pyridine catalyzes the conversions of alkyl N-sulfinylcarbamates to N,N'-bis(alkoxycarbonyl)sulfur diimides (FIG. 2; X=CO$_2$R), that in consequence very simple reagents can be used to aminate alkenes in their allylic positions (FIG. 4), and that excess pyridine must be avoided if N-sulfinylations of carbamate are to give high yields (FIGS. 5 and 6).

What is claimed is:

1. A method of preparing an allylic amine having the structure:

wherein R$_1$, R$_2$, R$_3$, R$_4$ and R$_5$ are each independently hydrogen, halogen, cyano, nitro, dialkylamino, alkoxy, aryloxy, alkoxycarbonyl, aryloxycarbonyl, alkylmercapto, arylmercapto, linear or branched chain alkyl, acyl, arylalkyl or aryl;

wherein each alkyl or arylalkyl if present is independently unsubstituted or substituted by fluoro, cyano, nitro, linear or branched chain acyl, dialkylamino, alkoxy, aryloxy, alkoxycarbonyl, aryloxycarbonyl, alkylmercapto, or arylmercapto;

wherein each aryl if present is independently unsubstituted or substituted by fluoro, cyano, nitro, linear or branched chain alkyl, acyl, dialkylamino, alkoxy, aryloxy, alkoxycarbonyl, aryloxycarbonyl, alkylmercapto, or arylmercapto;

wherein each of R$_1$, R$_2$, R$_3$, R$_4$ and R$_5$ optionally is covalently bonded linking pairwise a suitable atom from each to form from 0 to about 10 rings, wherein each ring contains between about four and about twelve atoms; which comprises:

(a) treating a compound having the structure:

with a sulfur diimide having the structure:

wherein R is substituted or unsubstituted linear or branched chain alkyl, arylalkyl or aryl; wherein the sulfur diimide is formed in situ by reacting a primary carbamate having the structure:

with a thionyl halide having the formula $SOM_2$, wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

2. The method of claim 1 wherein M is Cl and R is methyl.

3. The method of claim 1 wherein the base is an organic amine.

4. The method of claim 3 wherein the organic amine is pyridine.

5. The method of claim 3 wherein the organic amine is present in a 102 to 125 mole percent excess with respect to the primary carbamate.

6. The method of claim 5 wherein the organic amine is present in a 105 mole percent excess with respect to the primary carbamate.

7. A method of preparing an allylic amine having the structure:

wherein $R_1$, $R_2$ and $R_3$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, alkylmercapto, arylmercapto or aryl;

wherein $R_4$ and $R_5$ are each independently hydrogen, substituted or unsubstituted linear or branched chain alkyl or aryl; which comprises:

(a) reacting a compound having the structure:

with a sulfur diimide having the structure:

wherein R is substituted or unsubstituted, linear or branched chain alkyl, arylalkyl or aryl; wherein the sulfur diimide is formed in situ by reacting a primary carbamate having the structure:

with a thionyl halide having the formula $SOM_2$, wherein M is Br, Cl, F or I, in the presence of a base, to form an intermediate;

(b) hydrolyzing the intermediate formed in step (a) to form an allylic carbamate having the structure:

and (c) saponifying and decarboxylating the allylic carbamate formed in step (b) to form the allylic amine.

8. The method of claim 7 wherein M is Cl and R is methyl.

9. The method of claim 7 wherein the base is an organic amine.

10. The method of claim 9 wherein the organic amine is pyridine.

11. The method of claim 9 wherein the organic amine is present in a 102 to 125 mole percent excess with respect to the primary carbamate.

12. The method of claim 11 wherein the base is present in a 105 mole percent excess with respect to the primary carbamate.

13. A method of preparing an allylic amine having the structure:

wherein X, Y, and Z are each independently C, N, O, or S; wherein $R_1$, $R_2$, $R_3$, $R_4$, $R_5$, $R_6$, and $R_7$ are each independently hydrogen, halogen, cyano, nitro, substituted or unsubstituted linear or branched chain alkyl, acyl, diakylamino, alkoxy, aryloxy, alkoxycarbonyl, aryloxycarbonyl, or aryl;

wherein when X is O or S, $R_2$ and $R_3$ are absent;
wherein when Y is O or S, $R_4$ and $R_5$ are absent;
wherein when Z is O or S, $R_6$ and $R_7$ are absent;
wherein when X is N, $R_2$ is absent;
wherein when Y is N, $R_4$ is absent;
wherein when Z is N, $R_6$ is absent;
wherein i, j, and k are each independently 1 or 2;
wherein i+j+k equals 3 or 4;
wherein $R_8$ and $R_9$ are each independentiy hydrogen, substituted or unsubstituted linear or branched chain alkyl or aryl; which comprises:

a. treating a compound having the structure:

with a sulfur diimide having the structure:

wherein R is a substituted or unsubstituted linear or branched chain alkyl, arylalkyl, or aryl; wherein the sulfur diimide is formed in situ by reacting a primary carbamate having the structure:

with a thionyl halide having the formula $SOM_2$, wherein M is Br, Cl, F, or I, in the presence of a base, to form an intermediate;

b. hydrolyzing the intermediate formed in step a to form an allylic carbamate having the structure:

and;

c. saponifying and decarboxylating the allylic carbamate formed in step b to form the allylic amine.

14. The method of claim 13, wherein X, Y, and Z are C.

15. The method of claim 13, wherein M is Cl and R is methyl.

16. The method of claim 13, wherein the base is an organic amine.

17. The method of claim 16, wherein the organic amine base is pyridine.

18. The method of claim 16, wherein the organic amine base is present in a 102 to 125 mole percent excess with respect to the primary carbamate.

19. The method of claim 18, wherein the organic amine base is present in a 105 mole percent excess with respect to the primary carbamate.

20. A method of preparing an allylic amine having the structure:

wherein X, Y, and Z are each independently C, N, O, or S;

wherein $R_1$, $R_2$, $R_3$, $R_4$, $R_5$, $R_6$, and $R_7$ are each independently hydrogen, halogen, cyano, nitro, substituted or unsubstituted linear or branched chain alkyl, acyl, dialkylamino, alkoxy, aryloxy, alkoxycarbonyl, aryloxycarbonyl, or aryl;

wherein when X is O or S, $R_1$ and $R_2$ are absent;
wherein when Y is O or S, $R_3$ and $R_4$ are absent;
wherein when Z is O or S, $R_5$ and $R_6$ are absent;
wherein when X is N, $R_2$ is absent;
wherein when Y is N, $R_4$ is absent;
wherein when Z is N, $R_6$ is absent;
wherein i, j, and k are each independently 1 or 2;
wherein i+j+k equals 3 or 4;

wherein $R_8$ and $R_9$ are each independently hydrogen, substituted or unsubstituted linear or branched chain alkyl or aryl; which comprises:

a. treating a compound having the structure:

with a sulfur diimide having the structure:

wherein R is a substituted or unsubstituted linear or branched chain alkyl, arylalkyl, or aryl; wherein the sulfur diimide is formed in situ by reacting a primary carbamate having the structure:

with a thionyl halide having the formula $SOM_2$, wherein M is Br, Cl, F, or I, in the presence of a base, to form an intermediate;

b. hydrolyzing the intermediate formed in step a to form an allylic carbamate having the structure:

and;

c. saponifying and decarboxylating the allylic carbamate formed in step b to form the allylic amine.

21. The method of claim 20, wherein X, Y, and Z are C.

22. The method of claim 20, wherein M is Cl and R is methyl.

23. The method of claim 20, wherein the base is an organic amine.

24. The method of claim 23, wherein the organic amine base is pyridine.

25. The method of claim 23, wherein the organic amine base is present in a 102 to 125 mole percent excess with respect to the primary carbamate.

26. The method of claim 25, wherein the organic amine base is present in a 105 mole percent excess with respect to the primary carbamate.

* * * * *